US010138545B2

(12) United States Patent
Young

(10) Patent No.: US 10,138,545 B2
(45) Date of Patent: Nov. 27, 2018

(54) PROCESS FOR THE REMOVAL OF CONTAMINANTS FROM SPUTTERING TARGET SUBSTRATES

(71) Applicant: SCI ENGINEERED MATERIALS, INC., Columbus, OH (US)

(72) Inventor: Jeremy R. Young, Gahanna, OH (US)

(73) Assignee: SCI ENGINEERED MATERIALS, INC., Columbus, OH (US)

( * ) Notice: Subject to any disclaimer, the term of this patent is extended or adjusted under 35 U.S.C. 154(b) by 109 days.

(21) Appl. No.: 15/422,666

(22) Filed: Feb. 2, 2017

(65) Prior Publication Data
US 2017/0226628 A1    Aug. 10, 2017

Related U.S. Application Data

(60) Provisional application No. 62/291,962, filed on Feb. 5, 2016.

(51) Int. Cl.
| | | |
|---|---|---|
| C23C 14/34 | (2006.01) |
| B08B 3/10 | (2006.01) |
| B08B 3/08 | (2006.01) |
| B24B 7/22 | (2006.01) |
| G01N 23/223 | (2006.01) |
| C11D 11/00 | (2006.01) |
| C23C 22/00 | (2006.01) |

(52) U.S. Cl.
CPC ............ *C23C 14/3414* (2013.01); *B08B 3/10* (2013.01); *B24B 7/22* (2013.01); *C11D 11/0041* (2013.01); *C23C 22/00* (2013.01); *G01N 23/223* (2013.01)

(58) Field of Classification Search
CPC ......... B08B 3/10; B24B 7/22; C11D 11/0041; C23C 14/3414; C23C 22/00; G01N 23/223
See application file for complete search history.

(56) References Cited

U.S. PATENT DOCUMENTS

| | | | | |
|---|---|---|---|---|
| 4,764,260 A * | 8/1988 | Gay | .......................... | C25D 5/14 |
| | | | | 205/178 |
| 5,300,187 A * | 4/1994 | Lesk | ................. | H01L 21/02046 |
| | | | | 134/2 |
| 5,836,506 A * | 11/1998 | Hunt | .................... | B23K 20/023 |
| | | | | 228/172 |
| 6,063,254 A * | 5/2000 | Rosenberg | .......... | C23C 14/3414 |
| | | | | 205/398 |
| 8,292,698 B1 * | 10/2012 | Shih | ........................ | B24C 1/003 |
| | | | | 451/37 |
| 8,988,755 B2 * | 3/2015 | McCabe | ................... | B60R 1/08 |
| | | | | 359/245 |

(Continued)

FOREIGN PATENT DOCUMENTS

| | | | |
|---|---|---|---|
| JP | 09102126 A | * | 4/1997 |
| JP | H 09-102126 A | | 4/1997 |

*Primary Examiner* — Marc Carlson
(74) *Attorney, Agent, or Firm* — Hudak, Shunk & Farine Co., LPA

(57) ABSTRACT

The present invention provides a process for the removal of contaminants on a spent sputtering target used in Plasma Vapor Deposition by the steps of grit abrasion, organic solvent cleaning, and being subjected to an electric field in an acidic bath including a surfactant, and followed by subsequent water and air rinse and further grit abrasion. Removal of the contaminants is verified by spectroscopy.

18 Claims, 1 Drawing Sheet

(56) References Cited

U.S. PATENT DOCUMENTS

| | | | |
|---|---|---|---|
| 2005/0172984 A1* | 8/2005 | Schweitzer | B08B 7/0092 |
| | | | 134/26 |
| 2007/0012658 A1* | 1/2007 | Mize | B08B 3/08 |
| | | | 216/52 |
| 2011/0117338 A1* | 5/2011 | Poquette | C23C 18/1644 |
| | | | 428/213 |

* cited by examiner

PROCESS FOR THE REMOVAL OF CONTAMINANTS FROM SPUTTERING TARGET SUBSTRATES

FIELD OF THE INVENTION

This present invention relates to a process for the removal of contaminants, and more particularly of contaminants including chromium, and potentially also one or more of nickel or vanadium or alloys thereof, from substrates, and in particular sputtering target substrates, such as spent targets or recycled targets specifically including ruthenium, and alloys containing ruthenium.

BACKGROUND OF THE INVENTION

The present invention provides a process for the removal of metal contaminants that can be generated on a metal substrate, for example, on a sputtering target during the process of plasma generated thin film formation.

It is known in certain display and/or photonic technologies that metal substrates used for example for magnetic or plasma generated deposition, can be subjected to the presence of additional material that might be present in the form of additional material layers, and that during the deposition process, targets or substrates down line can end up with an undesirable contamination. An example of a patent that discusses the technology involved is U.S. Pat. No. 8,988,755 fully incorporated herein by reference, and which relates to a variable reflectance electro-optic vehicular rear-view mirror having a series of functional thin-film coatings laid down, for example by physical vapor, plasma, or magnetron deposition. In the manufacture of such articles, there exists the possibility of cross-contamination of the targets as the article of manufacture travels through production. The present invention is intended as a means of allowing such targets to be repressed or post processed for re-use.

SUMMARY OF THE INVENTION

In accordance with the process of the present invention, the contaminated substrate or sputtering target is cleaned mechanically, such as by abrasion, followed by cleaning with a solvent that includes an $C_{1-6}$ alcohol or ketone, and preferably a $C_{1-3}$ alcohol or ketone; followed by immersion in a caustic bath, which is acidic having a pH of from 1 to 4 and further including a surfactant, while the substrate is directly or indirectly subjected to an electric field by means of application of the field across the substrate or to a container in which the substrate is contained assuming grounding issues are addressed. Following a rinse with water and air, a second mechanical abrasion step is performed and a verification or qualification step is performed, such as spectroscopy to insure that the substrate has been cleaned of the contaminants.

DETAILED DESCRIPTION OF THE DRAWINGS

Figures 1, 2, 3:
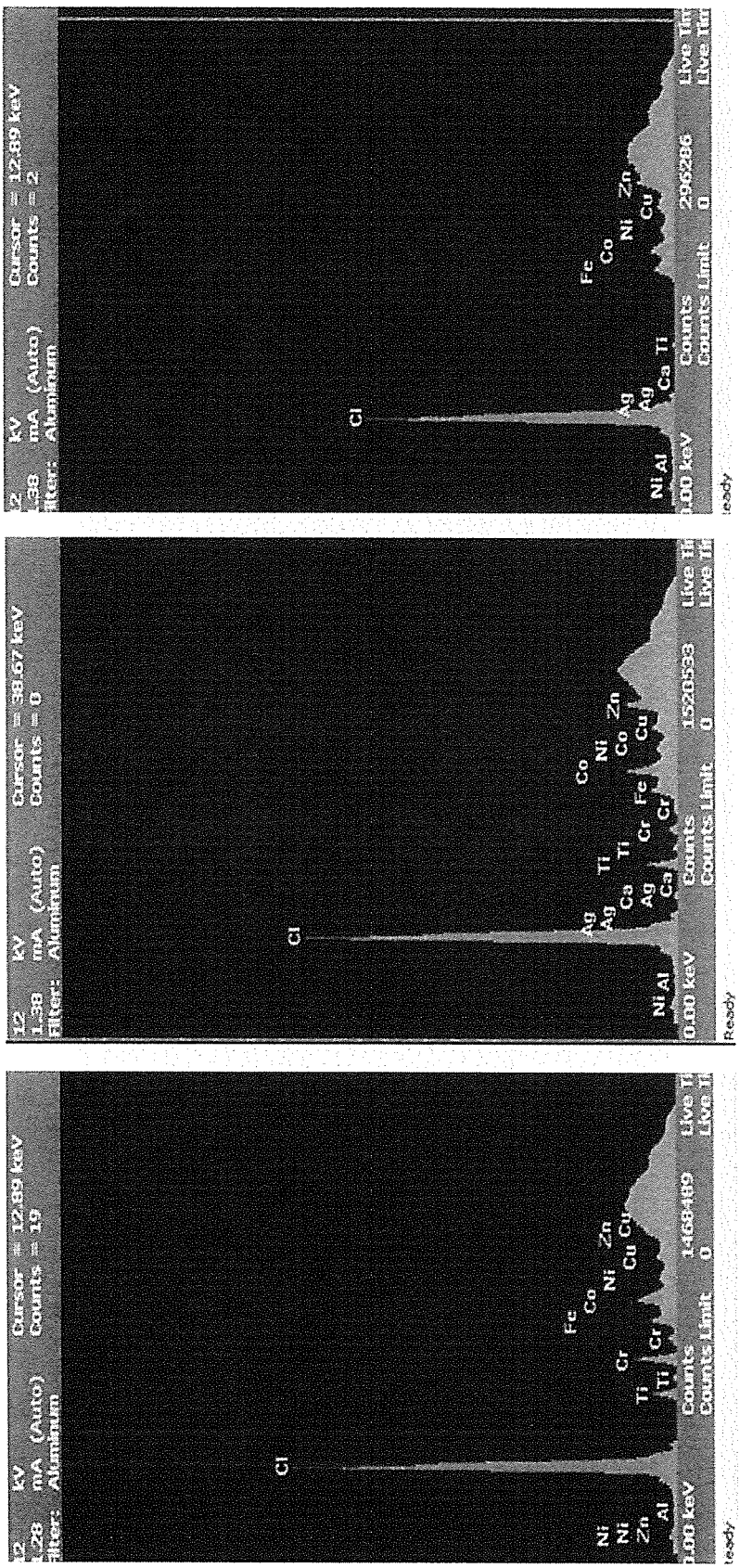
FIG. 1 is an XRF image showing a contaminated sputtering target prior to cleaning in accordance with the present invention.
FIG. 2 is an XRF image following grit blasting of the sputtering target of FIG. 1.
FIG. 3 is an XRF image following the completion of the method of the present invention of the target of FIG. 1.

FIG. 1 illustrates a spent sputtering target using X-Ray Fluoroscopy (XRF) imaging in which the chromium contaminants are marked. FIG. 2 illustrates XRF images of the target of FIG. 1 in which the target has been subjected to grit blasting in accordance with a first step of the process, but illustrating that the spent target is still contaminated by chromium, while FIG. 3 is an XRF image of the spent sputtering target following the complete process and illustrating the target is now free of chromium contaminants.

In accordance with the process of the present invention, the contaminated substrate, in particular, the spent ruthenium sputtering target, is cleaned mechanically, such as by abrasion and specifically by abrasive blasting including one or more of peen blasting, grit blasting, sand blasting, bead blasting, or bristle blasting, and advantageously with blasting at a typical pressure of 50-75 psi for a period until a visual surface change can be seen, such as a matte finish and with 180 aluminum oxide being a preferred abrasive. This step is followed by cleaning with a solvent that includes an $C_{1-6}$ alcohol or ketone, and preferably a $C_{1-3}$ alcohol or ketone including specifically one or more of isopropyl, ethanol, methanol, or acetone and preferably isopropyl alcohol, followed by immersion in a caustic bath optionally at a temperature of from room temperature to 100.degree. C., which is acidic bath including for example sulfuric or hydrochloric acid, the bath having a pH of from 2 to 4 and preferably 2.5 to 3.5, and further including a surfactant, which is for example dish soap, while the substrate is directly or indirectly subjected to an electric field such as a field of 120 volts at between 15 to 20 amps, by means of application of the field across the substrate or to a container in which the substrate is contained assuming that grounding issues are addressed, such as by immersion of the container in the bath. Following a rinse (optionally first with a isopropyl alcohol) and then with water and air, a second mechanical abrasion step preferably using the same abrasives and conditions but at a finer grit level is performed and a step is performed, such as spectroscopy and preferably via XRF (or any other spectroscopic technique available such as Arc Spark Spectroscopy, AES, XPS, or Surface Enhanced Raman Spectroscopy) to insure that the substrate has been cleaned of the contaminants.

Example 1 a spent target of ruthenium used for PVD deposition includes chromium contaminants as is shown in FIG. 1. This target is subjected to blasting at a rate of 70 psi for 10 minutes with 120 grit Aluminum Oxide grit. FIG. 2 shows that while some of the contaminants, including chromium are removed, the chromium remains a problem as a contaminant. This target is subsequently cleaned using isopropyl alcohol as a solvent followed by immersion in a caustic bath of sulfuric or hydrochloric acid at a pH of 2.8 to 3.2 which is subjected to a current of 120 volts at between 15-20 amps passed through the bath or to the container, but preferably through the bath. The target is subsequently rinsed using isopropyl alcohol and then distilled water and passed through an air stream to dry. A second abrasive step using similar conditions except for 180 grit aluminum oxide is applied. The target was subjected to XRF imaging and the resultant chromium free spent target is evidenced by the XRF image of FIG. 3.

Failed attempts to remove the contaminants from spent ruthenium targets at a similar level of contamination as is illustrated in FIG. 1 include 1) only a caustic bath of nitric acid at room temperature; 2) only grit blasting with 180 grit, and 220 grit aluminum oxide, and 180 grit silicon carbide; and 3) mechanical removal with 2" die grinder with 60, 80, and 120 grit aluminum oxide discs and 80 grit zirconium oxide. Each of these attempts did not result in satisfactory removal of the contaminants as was still evident on XRF imaging.

While in accordance with the patent statutes the best mode and preferred embodiment have been set forth, the scope of the invention is not limited thereto, but rather by the scope of the attached claims.

What is claimed is:

1. A method for the removal of chromium contaminants on a ruthenium sputtering target used in plasma vapor deposition including the steps of
    subjecting the ruthenium sputtering target to grit abrasion followed by an organic solvent cleaning to result in a pre-cleaned target,
    subjecting the pre-cleaned target to an electric field in an acidic bath including a surfactant, followed by subsequent water and air rinse.

2. A method as set forth in claim 1 wherein the target is subjected to a second grit abrasion following the water and air rinse.

3. A method as set forth in claim 1 wherein the removal of the chromium contaminants is verified by spectroscopy.

4. A method as set forth in claim 3 wherein the spectroscopy is XRF.

5. A method as set forth in claim 1 wherein one of 120 or 180 grit aluminum oxide is used.

6. A method as set forth in claim 2 wherein 120 grit aluminum oxide is used in the grit abrasion and 180 grit aluminum oxide is used in the second grit abrasion.

7. A method as set forth in claim 1 wherein the electric field is 120 volts which is applied to the ruthenium sputtering target wherein the ruthenium sputtering target is held in a container in the acidic bath and the electric field is applied to the bath.

8. A method as set forth in claim 1 wherein the electric field is 120 volts which is applied to the ruthenium sputtering target wherein the ruthenium sputtering target is held in a container in the acidic bath and the electric field is applied to the container which holds the sputtering target.

9. A method as set forth in claim 1 wherein the organic solvent is a C1-6 alcohol or ketone.

10. A method as set forth in claim 9 wherein the organic solvent is a C1-3 alcohol or ketone.

11. A method as set forth in claim 10 wherein the caustic bath is an acidic bath having a pH of from 1 to 4.

12. A method as set forth in claim 11 wherein the acidic bath has a pH of from 2.5 to 3.5.

13. A method as set forth in claim 11 wherein the caustic bath further includes a surfactant.

14. A method as set forth in claim 13 wherein the surfactant is dish soap.

15. A method as set forth in claim 1 wherein the caustic bath is at a temperature of from 22° to 100° C.

16. A method for the removal of chromium contaminants on a ruthenium substrate including the steps of
    subjecting the ruthenium substrate to grit abrasion using 120 to 180 grit aluminum oxide followed by an organic solvent cleaning to result in a pre-cleaned substrate having a matte finish, and the organic solvent comprising $C_{1-6}$ alcohol or ketone,
    subjecting the pre-cleaned substrate to an electric field at 50-150 volts in an acidic bath at a pH of 1-4 and including a surfactant, followed by subsequent water and air rinse; and subjecting the substrate to second grit abrasion using 120 to 180 grit aluminum oxide, following the water and air rinse.

17. A method as set forth in claim 16 wherein the removal of the chromium contaminants is verified by spectroscopy.

18. A method as set forth in claim 17 wherein the acidic bath is sulfuric or hydrochloric acid and the organic solvent is isopropyl alcohol.

* * * * *